US010357464B2

(12) United States Patent
Phan et al.

(10) Patent No.: US 10,357,464 B2
(45) Date of Patent: *Jul. 23, 2019

(54) METHODS FOR DELIVERING VOLATILE ANESTHETICS FOR REGIONAL ANESTHESIA AND/OR PAIN RELIEF

(75) Inventors: Phillip C. Phan, Houston, TX (US); Allen W. Burton, Houston, TX (US)

(73) Assignee: The Board of Regents of the University of Texas System, Austin, TX (US)

( * ) Notice: Subject to any disclaimer, the term of this patent is extended or adjusted under 35 U.S.C. 154(b) by 141 days.

This patent is subject to a terminal disclaimer.

(21) Appl. No.: 13/183,257

(22) Filed: Jul. 14, 2011

(65) Prior Publication Data
US 2011/0269843 A1    Nov. 3, 2011

Related U.S. Application Data

(62) Division of application No. 11/858,497, filed on Sep. 20, 2007, now abandoned.

(60) Provisional application No. 60/947,219, filed on Jun. 29, 2007, provisional application No. 60/846,293, filed on Sep. 20, 2006.

(51) Int. Cl.
| | | |
|---|---|---|
| *A01N 43/00* | (2006.01) | |
| *A61K 31/33* | (2006.01) | |
| *A61K 31/02* | (2006.01) | |
| *A61K 9/00* | (2006.01) | |
| *A61K 9/08* | (2006.01) | |
| *A61K 31/07* | (2006.01) | |

(52) U.S. Cl.
CPC ............ *A61K 31/02* (2013.01); *A61K 9/0019* (2013.01); *A61K 9/08* (2013.01); *A61K 31/07* (2013.01)

(58) Field of Classification Search
None
See application file for complete search history.

(56) References Cited

U.S. PATENT DOCUMENTS

| | | | |
|---|---|---|---|
| 3,720,587 A | 3/1973 | Croix | 203/58 |
| 4,109,651 A | 8/1978 | Steigerwald | 128/145.8 |
| 4,453,951 A | 6/1984 | Ohno | 51/307 |
| 4,622,219 A * | 11/1986 | Haynes | A61K 9/1075 424/450 |
| 4,744,989 A | 5/1988 | Payne et al. | 424/490 |
| 4,794,921 A | 1/1989 | Lindkvist | 128/203.29 |
| 4,879,062 A | 11/1989 | Moore | 252/315.1 |
| 5,114,714 A | 5/1992 | Young et al. | 424/400 |
| 5,114,715 A | 5/1992 | Young et al. | 424/400 |
| 5,227,165 A * | 7/1993 | Domb et al. | 424/450 |
| 5,230,778 A | 7/1993 | Gavlin et al. | 203/58 |
| 5,235,971 A | 8/1993 | Falb et al. | 128/203.14 |
| 5,552,404 A | 9/1996 | Chang et al. | 514/255.04 |
| 5,568,910 A | 10/1996 | Koehler et al. | 251/83 |
| 5,677,290 A | 10/1997 | Fukunaga | 514/46 |
| 5,679,650 A | 10/1997 | Fukunaga et al. | 514/46 |
| 5,690,968 A | 11/1997 | Ross et al. | 424/718 |
| 5,854,249 A | 12/1998 | Chang et al. | 514/252.13 |
| 5,874,469 A | 2/1999 | Maniar et al. | 514/550 |
| 5,919,826 A | 7/1999 | Caruso | 514/629 |
| 5,942,497 A | 8/1999 | Fukunaga et al. | 514/46 |
| 5,976,072 A | 11/1999 | Greenberg | 600/120 |
| 6,248,788 B1 | 6/2001 | Robbins et al. | 514/627 |
| 6,669,954 B2 | 12/2003 | Crison et al. | 424/456 |
| 6,706,034 B1 | 3/2004 | Bhat | 604/890.1 |
| 6,770,636 B2 | 8/2004 | Fuchs et al. | 514/183 |
| 6,830,581 B2 | 12/2004 | Magers | 607/105 |
| 6,869,440 B2 | 3/2005 | Dobak | 607/105 |
| 2001/0036943 A1 * | 11/2001 | Coe et al. | 514/220 |
| 2002/0068764 A1 * | 6/2002 | Franks et al. | 514/653 |
| 2003/0173287 A1 | 9/2003 | Johnston et al. | 210/496 |
| 2003/0181426 A1 | 9/2003 | Eisenach | 514/161 |
| 2003/0185761 A1 * | 10/2003 | Dugger, III | A61K 9/0056 424/43 |
| 2003/0212123 A1 | 11/2003 | DeMello et al. | 514/411 |
| 2005/0129754 A1 | 6/2005 | Gray et al. | 424/450 |
| 2006/0067952 A1 | 3/2006 | Chen | 424/400 |
| 2006/0198891 A1 | 9/2006 | Ravenelle et al. | 424/486 |
| 2008/0234389 A1 | 9/2008 | Mecozzi et al. | 514/722 |
| 2011/0039944 A1 | 2/2011 | Capelli et al. | |

(Continued)

FOREIGN PATENT DOCUMENTS

| | | |
|---|---|---|
| CA | 2584619 | 5/2006 |
| CA | 2591715 | 6/2006 |

(Continued)

OTHER PUBLICATIONS

Smith et al. (Contemp Top Lab Animal Sci, vol. 39, No. 6, abstract; 2000).*
Fassoulaki et al., "Skin application of isoflurane attenuates responses to mechanical and an electrical stimulation," Can J Anaesth 1998 / 45:12 / pp. 1151-1155.*
Lida et al., "Isoflurane and Sevoflurane Induce Vasodilation of Cerebral Vessels via ATP-sensitive K+ Channel Activation," Anesthesiology 1998; 89:954-960.*
Abe, "Vasodilators during cerebral aneurysm surgery," Can J Anaesth 1993/40:8/pp. 775-790.*
"Anesthesia," retrieved from http://www.thefreedictionary.com/anesthesia, retrieved on Oct. 23, 2010.

(Continued)

*Primary Examiner* — Jared Barsky
(74) *Attorney, Agent, or Firm* — Parker Highlander PLLC

(57) ABSTRACT

The present invention provides methods for reducing pain in a subject in need of such pain reduction by delivering, e.g., intrathecally or epidurally, a volatile anesthetic such as a halogenated ether compound in an amount effective to reduce pain. Chronic or acute pain may be treated, or the anesthetic may be delivered to the subject to anesthetize the subject prior to a surgery. In certain embodiments, isoflurane, halothane, enflurane, sevoflurane, desflurane, methoxyflurane, xenon, and mixtures thereof may be used. Dosing regimens including a one-time administration, continuous and/or periodic administration are contemplated.

10 Claims, 4 Drawing Sheets

(56) References Cited

U.S. PATENT DOCUMENTS

| | | | |
|---|---|---|---|
| 2011/0159078 A1 | 6/2011 | Burton et al. | |
| 2012/0171281 A1 | 7/2012 | Spakevicius et al. | |
| 2013/0273141 A1 | 10/2013 | Burton et al. | |

FOREIGN PATENT DOCUMENTS

| | | |
|---|---|---|
| EP | 0 711 289 | 8/2000 |
| EP | 1854484 | 11/2007 |
| GB | 2350297 | 11/2000 |
| JP | 8-509712 | 10/1996 |
| WO | WO 1994/023727 | 10/1994 |
| WO | WO 96/16063 | 5/1996 |
| WO | WO 98/014174 | 4/1998 |
| WO | WO 98/17268 | 4/1998 |
| WO | WO 99/03459 | 1/1999 |
| WO | WO 99/49854 | 10/1999 |
| WO | WO 01/82952 | 11/2001 |
| WO | WO 02/085308 | 10/2002 |
| WO | WO 03/059347 | 7/2003 |
| WO | WO 03/077939 | 9/2003 |
| WO | WO 04/014311 | 2/2004 |
| WO | WO 2004/032858 | 4/2004 |
| WO | WO 04/087158 | 10/2004 |
| WO | WO 04/100868 | 11/2004 |
| WO | WO 04/103299 | 12/2004 |
| WO | WO 05/016323 | 2/2005 |
| WO | WO 05/016955 | 2/2005 |
| WO | WO 05/021756 | 3/2005 |
| WO | WO 05/031000 | 4/2005 |
| WO | WO 2006-054652 | 5/2006 |
| WO | WO 2006-064886 | 6/2006 |
| WO | WO 2006-088088 | 8/2006 |

OTHER PUBLICATIONS

Anderson et al., "Isoflurane blocks LTP of hippocampal CA1 neurons at concentrations that block recall during anesthesia," 30th Annual Meeting of the Society of Neuroscience, New Orleans, LA, Nov. 2000.

ASA Newsletter, "FAER announce 1997 new investigator award recipients," 61, 1997.

Bacon et al., "Regional anesthesia and chronic pain management in the 1920s and 1930s. The influence of the American Society of Regional Anesthesia," Reg. Anesth., 20:185-92, 1995 (Abstract only).

Breen and Park, "General anesthesia versus regional anessthesia," Int. Anesthesiol. Clin., 40:61-71, 2002.

Campagna et al., "Mechanisms of actions of inhaled anesthetics," N. Engl. J. Med., 348:2110-24, 2003.

Chai et al., "Epidural anesthetic effects of emulsified isoflurane (8%, v/v): a puiolet study in rabbits," ASA, A743, 2006.

Chaplan et al., "Quantitative assessment of tactile allodynia in the rat paw," J. Neurosci. Methods, 53:55-63, 1994.

Delgado-Herrera et al., "Sevoflurance: approaching the ideal inhalational anesthetic, a pharmacologic, pharmacoeconomic, and clinical review," CNS Drug Rev., 7:48-120, 2001.

Dirt et al., "Effect of COX-1 and COX-2 inhibition on induction and maintenance of carrageenan-evoked thermal hyperalgesia in rats," J. Pharmacol. Exp. Ther., 285:1031-8, 1998.

Eckenoff and Eckenoff, "Quantitative autoradiography of halothane binding in rat brain," The Journal of Pharmacology and Experimental Therapeutics, 285:371-376, 1998.

Galinksky and Svensson, "Basic pharmacokinetics and pharmacodynamics," In: Remingtion: the Science and Practice of Pharmacy, Baltimore, Lippincott Williams & Wilkins, pp. 1171, 2006.

Garcia-Fernandez et al., "Clinical actions of subarachnoid sevoflurane administration in vivo: a study in dogs," British Journal of Anaesthesia, 95:530-534, 2005.

Hargreaves et al., "A new and sensitive method for measuring thermal nociception in cutaneous hyperalgesia," Pain, 32:77-88, 1988.

Haseneder et al., "Isoflurane reduces glutamatergic transmission in neurons in the spinal cord superficial dorsal horn: evidence for a presynaptic site of an analgesic action," Anesth. Analg., 98:1718-23, 2004.

Hemmings et al., "The general anesthetic isofluran depresses synaptic vesicle exocytosis," Mole. Pharmacol., 67:1591-1599, 2005.

Hyderally, "Complications of spinal anesthesia," Mt. Sinai. J. Med., 69:55-56, 2002.

Johnson, "Potential neurotoxicity of spinal anesthesia with lidocaine," Mayo Clinic Proceedings, 75:921-932, 2000.

Kim and Chung, "An experimental model for peripheral neuropathy produced by segmental spinal nerve ligation in the rat," Pain, 50:355-363, 1992.

Koblin, Donald D. "Mechanisms of Action," In Ronald D. Miller, (Ed). Anesthesia. 4th Edition. Chapter 5. pp. 67-99. New York: Churchill Livingstone Inc. 1994.

Kruer et al., "Application of Bispectral Index ® and Narcotrend ® index to the measurement of the electroencephalographic effects of isoflurane with and without burst suppression," Anesthesiology, 101:847-54, 2004.

Liu and McDonald, "Current issues in spinal anesthesia," Anesthesiology, 94:888-906, 2001.

Mathias et al., "Intravenous isoflurane in lipid emulsion promotes cardiovascular and respiratory stability experimental model," Revista Brasileira de Anestesiologia, 54:650-662, 2004.

Gozzani, "New pharmacotechnique for old agents," Revista Brasileira de Anestesiologia, 54:623-624, 2004.

Matute and Lopez-Garcia, "Characterization of sevoflurane effects on spinal somato-motor nociceptive and non-nociceptive transmission in neonatal rat spinal cord: an electrophysiological study in vitro," Neuropharmacology, 44:811-816, 2003.

Moller et al., "Long-term postoperative cognitive dysfunction in the elderly ISPOCD1 study. ISPOCD investigators. International Study of Post-Operative Cognitive Dysfunction," Lancet, 351:857-861, 1998.

Moraca et al., "The role of epidural anesthesia and analgesia in surgical practice," Ann. of Surgery, 238:663-673, 2003.

Murray, "The future of anesthesia delivery: from art-based science to science-based art," ASA Newsletter, 68, 2004.

Office Action, issued in U.S. Appl. No. 11/858,497, dated Jun. 28, 2010.

Office Action, issued in U.S. Appl. No. 11/858,497, dated Oct. 29, 2010.

Ouellette and Ouellette, "Regional Anesthesia: is it safer?," CRNA, 6:70-78, 1995.

PCT International Search Report and Written Opinion, issued in International Application No. PCT/US2007/079097, dated May 7, 2008.

Rasmussen et al., "Does anaesthesia cause postoperative cognitive dysfunction? A randomised study of regional versus general anaesthesia in 438 elderly patients," Acta Anaesthesiologica Scandinavica, 47:260-266, 2003.

Remington: The Science and Practice of Pharmacy, 20th Ed., Baltimore, MD: Lippincott Williams & Wilkins, 2000, pp. xiv-xv, (Table of Contents).

Robinson and Zhuo, "Pharmacological interventions at the spinal cord," Methods in Molecular Medicine, 84:217-222, 2003.

Rogers et al., "Knowledge and communication difficulties for patients with chronic heart failure: qualitative study," BMJ, 321:605-607, 2000.

Sevorane, Information for Health Professionals Presentation, www.medsafe.govt.nz/profs, Apr. 27, 2005.

Sorkin et al., "Pain models display differnetial sensitivity to Ca (2+-) permeable non-NMDA glutamate receptor antagonists," Anesthesiology, 95:965-973, 2001.

Sumikura and Arendt-Nielsen, "MAC reduction after intrathecal coadministration of GABA (A) agonist and glutamate antagonist in rats," J. Anesth., 17:92-97, 2003.

Takenoshita et al., "Halothane suppresses inhibitory monosynaptic transmission," Progress in Anesthetic Mechanism, 3:326-329, 1995.

Ting, "Low flow anesthesia: advantages and disadvantages, Part 1," Clinical Window, 1-4, 2003.

(56) References Cited

OTHER PUBLICATIONS

Tung, "New anesthesia techniques," *Thorac. Surg. Clin.*, 15:27-38, 2005.
Yaksh and Rudy, "Chronic catheterization of the spinal subarachnoid space," *Physiol. Behav.*, 17:1031-6, 1976.
Yaksh et al., "An automated flinch detecting system for use in the formalin nociceptive bioassay," *J. Appl. Physiol.*, 90:2386-2402, 2001.
Yamauchi et al., "Inhibitory action of sensory transmission by inhalational anesthetics in the spinal cord (English Abstract)," *Masui.*, 52:240-50, 2003.
Zhang et al., "Both cerebral GABA (A) receptors and spinal GABA (A) receptors modulate the capacity of isoflurane to produce immobility," *Anesth. Analg.*, 92:1585-9, 2001.
Zhang et al., "Glycine receptors mediate part of the immobility produced by inhaled anesthetics," *Anesth. Analg.*, 96:97-101, 2003.
"Recommended anesthetic method : Anesthesia of abdominal operation. Inhalation anesthesia," *The Journal of Japan Society for Clinical Anesthesia*, 16(3):214-217, 1996.
De Larminat et al., "Role of prostaglandins and nitric oxide on halothane-induced arteriolar dilatation in rat diaphragm," *British Journal of Anaesthesia*, 77:232-237, 1996.
Haynes et al., "Long duration local anesthesia with lecithin-coated microdroplets of methoxyflurane: studies with human skin," *Regional Anesthesia*, 16:173-180, 1991.
Office Action issued in European Application No. 07842927.1, dated Oct. 22, 2012.
Office Action issued in Indian Application No. 1757/DELNP/2009, dated Sep. 8, 2014.
Office Action issued in Japanese Application No. 2009-529406, dated Oct. 3, 2012.
Office Action issued in Japanese Application No. 2013-211544, dated Nov. 26, 2014.
Fassoulaki et al., "Local application of volatile anesthetics attenuates the response to a mechanical stimulus in humans," *Can. J. Anesth.*, 52(9):951-957, 2005.
Fassoulaki et al., "Percutaneous loss of desflurane, isoflurane, and halothane in humans," *Anesthesiology*, 74(3):479-483, 1991.
Skouteri et al., "Local application of halothane, isoflurane or sevoflurane increases the response to an electrical stimulus in humans," *Acata Anaesthesia Belg.*, 58(3):169-75, 2007.
Fassoulaki et al., "Skin application of isoflurane attenuates the responses to a mechanical and an electrical stimulation," *Can. J. Anaesth.*, 45(12):1151-1155, 1998.
Ardente et al., "Vehicle effects on in vitro transdermal absorption of sevolurane in the bullfrog, *Rana catesbeiana*," *Environmental Toxicology and Pharmacology*, 25:373-379, 2008.
Fast et al., "Fluoropolymer-based emulsions for the intravenous delivery of sevoflurane," *Anesthesiology*, 109:651-6, 2008.
Office Communication issued in U.S. Appl. No. 12/863,757, dated Jun. 22, 2012.
Parlato et al., "Synthesis, characterization, and applications of hemifluorinated dibranced amphiphiles," *J. Org. Chem.*, 76:6584-6591, 2011.
Zhou et al., "The efficacy and safety of intravenous emulsified isoflurane in rats," *Anesth. Analg.*, 102:129-34, 2006.
Office Action issued in Japanese Application No. 2015-204185, dated May 10, 2017, and English language translation thereof.
"Cerebral aneurysms fact sheet," National Institute of Neurological Disorders and Stroke, 8 pages, date last modified May 10, 2017.

* cited by examiner

METHODS FOR DELIVERING VOLATILE ANESTHETICS FOR REGIONAL ANESTHESIA AND/OR PAIN RELIEF

The present application is a division of co-pending application Ser. No. 11/858,497, filed Sep. 20, 2007, which claims priority to U.S. Provisional Application No. 60/846,293 filed on Sep. 20, 2006, and U.S. Provisional Application No. 60/947,219 filed on Jun. 29, 2007, the entire contents of each of which are incorporated herein by reference in their entirety, without disclaimer.

BACKGROUND OF THE INVENTION

1. Field of the Invention

The present invention relates generally to the fields of anesthesia and pain management. More specifically, the present invention provides methods for reducing pain by regionally delivering a solution comprising a volatile anesthetic to a subject in need of pain reduction or anesthesia.

2. Description of Related Art

Millions of people suffer from pain. The pain may be minor, such as headaches, acute lower back pain, and acute muscle pain, or severe, such as chronic pain. Chronic pain may be associated with cancer treatment, HIV, diabetes, or other conditions. Chronic pain can be difficult to treat, with many chronic pain sufferers noting that their pain is not well controlled with current pain medications or that their medications have significant associated adverse effects (e.g., nausea and vomiting, dependence, tolerance, etc.).

In an attempt to address the problem of chronic pain management, intrathecal infusion pumps and neurostimulators have been developed. Intrathecal infusion pumps are aimed at continuous, or near continuous delivery of liquid anesthetic and/or analgesic agents. Many of these infusion pumps are totally implantable, which helps to reduce the risk of infection when compared to the long-term use of external systems. The infusion pump may also be programmable to allow patients or their clinicians to adjust dosing amounts or daily delivery schedule, helping to meet a patient's changing needs.

Neurostimulators are available in various forms and stimulate nerves to relieve pain. Both intrathecal pumps and neurostimulators have drawbacks, including the onset of tolerance, with the treatments becoming less effective over time. In addition, neither intrathecal infusion pumps nor neurostimulators are suitable for anesthetizing a patient prior to a surgery.

Various approaches for inducing anesthesia or analgesia are known. Delivery of a general anesthetic renders a patient unconscious and unaware of the surgery. In contrast, anesthetics may be applied regionally, for example, to the spine, epidurally, or near a nerve in a nerve block to anesthetize only a portion of the patient's body. For general anesthesia, delivery of a general anesthetic to a patient prior to surgery is typically performed using an initial i.v. injection of an anesthetic followed by intubation and administration of an inhalable anesthetic gas. It is worthwhile to note that the mechanism of action for general anesthesia is still not completely understood.

Considerable negative side effects may result from administration of general anesthesia. A large tube has to be placed into the trachea, which can result in trauma to the upper airway. Many patients report postoperative hoarseness and tenderness of the mouth and throat. In addition, the large amount of gases required to flood the body to reach the targeted organs can have an adverse affect on the non-targeted organs, especially the heart, with an increased risk of cardiopulmonary morbidity during general anesthesia. Especially in the elderly, there is substantial evidence for prolonged cognitive dysfunction following general anesthesia (Moller et al., 1998). Additionally, regional anesthetic techniques appear to lead to less overall morbidity and mortality from cardiopulmonary causes as compared to general anesthesia (Rasmussen et al., 2003; Rogers et al., 2000)

Clearly, there exists a need for improved methods for pain management and regional anesthesia. Further, there exists a need for additional methods for delivering an anesthetic, such as a halogenated ether or a volatile anesthetic, for treating pain or for use in a surgical procedure.

SUMMARY OF THE INVENTION

The present invention overcomes limitations in the prior art by providing new methods for administering anesthetics and reducing pain in a subject, such as a human or animal patient or laboratory animal such as a mouse or rat, in need of such pain reduction. The methods preferably comprise the local or regional delivery, such as intrathecal or epidural delivery, of a volatile anesthetic in an aqueous based solution to the subject in an amount effective to reduce chronic or acute pain. In certain embodiments, and the anesthetic may be delivered to the subject to anesthetize the subject prior to a surgery. It should be understood, that as used herein, the phrase "pain reduction" is intended to cover pain reduction as a result of anesthesia, analgesia, and/or the inhibition of neural impulses involved in pain perception, e.g., via partial nerve conduction block.

The present invention has several substantial advantages over previously used methods for regional anesthesia. These advantages include: (1) the volatile anesthetics of the present invention are rapidly titratable, thus administration of a volatile anesthetic according to the present invention can result in a very quick onset of analgesia or regional anesthesia. (2) The present invention allows for the quick dissipation of anesthetics after administration; thus the anesthesia or analgesia may be rapidly ended. These properties are of particular value to a practitioner, as it may be desirable for a practitioner to quickly alter the dosing of a regional anesthesia or analgesia as desired. (3) Certain drugs presently used for regional anesthesia may not be effectively used on various individuals for a variety of reasons, including tolerance, drug interactions, paradoxical responses, etc. Additionally, (4) the volatile anesthetics of the present invention are generally non-opioid compounds, which provides various benefits for a practitioner, as opioids possess certain disadvantages, including tolerance, drug interactions, and dependence etc.

An aspect of the present invention relates to a method for reducing pain in a subject in need of such pain reduction comprising regionally or locally delivering to the subject a volatile anesthetic dissolved in a solution in an amount effective to reduce pain. In preferred embodiments, the anesthetic is delivered by routes other than intravenously in that intravenous delivery could potentially give rise to general anesthesia that, while not specifically excluded from the present invention, is not a preferred aspect. Preferred volatile anesthetics are the halogenated ether anesthetic dissolved in an aqueous, pharmaceutically acceptable solution. The anesthetic may preferably be delivered intrathecally, epidurally, or in a nerve block procedure, to relieve, for example, chronic pain or acute pain.

In certain embodiments, a volatile anesthetic in solution is delivered to anesthetize a portion of the subject prior to a surgery. In preferred embodiments, the volatile anesthetic is a halogenated volatile anesthetic selected from the group consisting of isoflurane, halothane, enflurane, sevoflurane, desflurane, methoxyflurane, and mixtures thereof, with isoflurane being particularly preferred. The solution, such as an isoflurane solution, may be prepared in a concentration of about 5 ng/ml solution to about 100, ng/ml solution. The solution may comprise from about 5% to about 75% v/v, from about 10% to about 50% v/v, or about 10% v/v anesthetic in solution. The anesthetic may be isoflurane and/or the solution may be artificial cerebrospinal fluid. When administered epidurally or intrathecally it is desirable to achieve a concentration of from about 250 ng/ml to about 50,000 ng/ml of active agent in the spinal fluid. The delivery of the active agent may be continuous, periodic, a one-time event, or the active agent may be both periodically administered and continuously administered to the subject on separate occasions. The reduction may comprise elimination of pain perception of a portion of the body of the subject.

Preferably, in that the solution is intended for parenteral administration, the aqueous solution comprising the volatile anesthetic is sterile. This can be achieved by ensuring that all starting materials are sterile and maintaining them under sterile conditions prior to administration. As for the underlying aqueous solution, the nature of the solution is not believed to be critical, and solutions such as normal saline or even solutions formulated to mimic natural body fluids, such as artificial cerebrospinal fluids, are contemplated. However, it is highly preferable to exclude oil-in-water emulsions, such as lipid emulsions, from inclusion in the solutions of the present invention.

Yet another aspect of the present invention involves a sealed container comprising an anesthetic solution of the present invention. The interior of the container may be sterile. The container may comprise a rubber stopper which can be easily pierced by an injection needle. The container may comprise the chamber portion of a syringe. The container may comprise a drip chamber. The drip chamber may be coupled to a catheter. The catheter may be an epidural catheter or an intrathecal catheter. The container may be a plastic bag, a glass bottle, or a plastic bottle. The container may be coupled to an infusion pump. The infusion pump may be an intrathecal pump, an epidural delivery infusion pump, or a patient control analgesia (PCA) pump. The infusion pump may be programmable.

The terms "inhibiting," "reducing," or "prevention," or any variation of these terms, when used in the claims and/or the specification includes any measurable decrease or complete inhibition to achieve a desired result.

The term "effective," as that term is used in the specification and/or claims, means adequate to accomplish a desired, expected, or intended result.

The use of the word "a" or "an" when used in conjunction with the term "comprising" in the claims and/or the specification may mean "one," but it is also consistent with the meaning of "one or more," "at least one," and "one or more than one."

It is contemplated that any embodiment discussed in this specification can be implemented with respect to any method or composition of the invention, and vice versa. Furthermore, compositions of the invention can be used to achieve methods of the invention.

Throughout this application, the term "about" is used to indicate that a value includes the inherent variation of error for the device, the method being employed to determine the value, or the variation that exists among the study subjects.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

DETAILED DESCRIPTION

Figure 1:
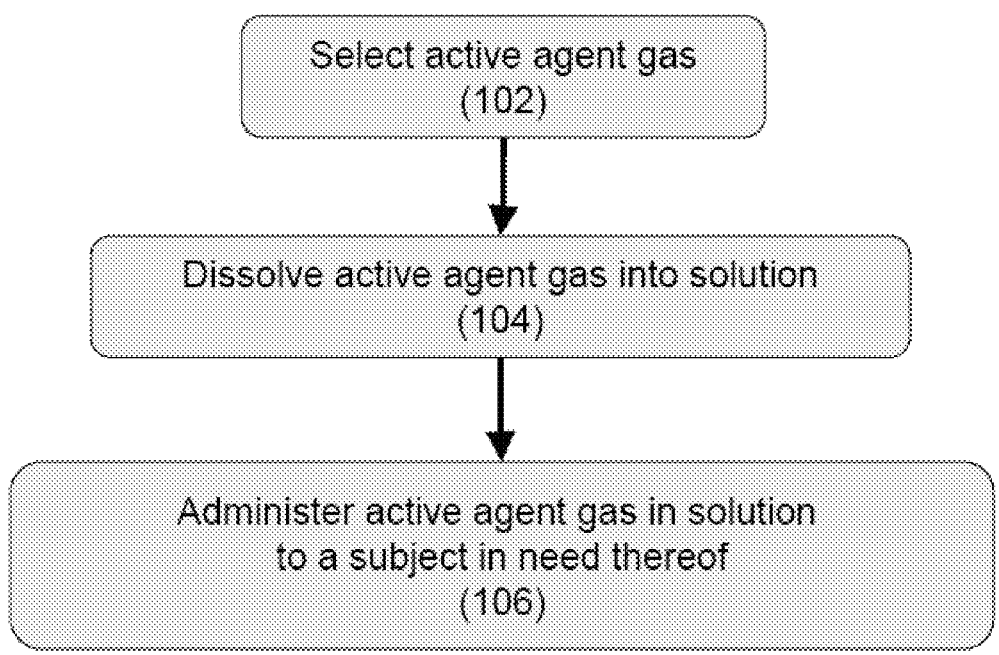
FIG. 1: A flowchart representing a general method for delivering an anesthetic gas to a subject.

The present invention provides methods for reducing pain in a subject in need of such pain reduction. Specifically, although volatile anesthetics are normally inhaled during a general anesthesia procedure, the inventors have discovered that volatile anesthetics may be dissolved in a solution and delivered regionally or locally (e.g., intrathecally, epidurally, or in a nerve block) to inhibit or block pain perception. In general, the methods may involve the delivery of a halogenated ether anesthetic to the subject in an amount effective to reduce pain. The present invention may be used for pain management of chronic or acute pain. In other embodiments, the anesthetic may be delivered to a subject to anesthetize at least a portion of the subject prior to a surgery.

Anesthetic Agents

In general, the halogenated ether anesthetics or volatile anesthetics suitable for use with the described methods include agents which, although often liquid at room temperature, are capable of easily being becoming gaseous or are already gaseous at room temperature and can reduce pain, e.g., without significant side effects. It may be desirable, for example, to select an anesthetic that is minimally metabolized by the body or is otherwise inert. In this way, liver and kidney toxicity may be minimized. Similarly, it may be desirable for the anesthetic to have a short half-life, or be fast acting to promote titratability (i.e., the subject can easily adjust the delivery amount for the amount of pain he or she is experiencing). An active agent gas that does not produce tolerance (unlike opioids or local anesthetic agents) or dependence (like opioids) may also be desirable.

Volatile anesthetics are a well known class of anesthetics which includes halogenated ether compounds, isoflurane, sevoflurane, halothane, enflurane, desflurane, methoxyflurane, and diethyl ethers. In certain embodiments xenon may also be used with the present invention. A single anesthetic or mixtures of the above anesthetics may be particularly suitable for use with the methods described herein.

In various embodiments, a gas anesthetic may used with the present invention. For example, the gas anesthetic may be dissolved in a solution according to the present invention and administered in a regional or local anesthesia procedure, such as an epidural, intrathecal, or nerve block procedure. Gas anesthetics other than halogenated anesthetics are contemplated, and examples or which include xenon, nitrous oxide, cyclopropane, and ether. In various embodiments, other biologically active gases (e.g., nitric oxide, etc.) may be delivered in a solution to a subject according to the present invention.

More than one anesthetic may be administered at one time, and different anesthetics may be administered at various times throughout a single treatment cycle. For example, 2, 3, 4 or more anesthetic agents may be simultaneously or repeatedly administered to a subject. When compounds are repeatedly administered to a subject, the duration between administration of compounds may be about 1-60 seconds, 1-60 minutes, 1-24 hours, 1-7 days, 1-6 weeks or more, or any range derivable therein. In some instances, it may be desirable to stage the delivery of different halogenated ether compounds depending on their physical and physiological properties.

Dosing

The amount of the anesthetic to be administered, e.g., intrathecally or epidurally, depends on the particular indication desired. For example, the dose will depend on the type of pain intended to be treated. The dose may be different, for instance, if the delivery of the anesthetic is intended to reduce chronic pain as opposed to acute pain. Similarly, the dose may be different if the active agent will be used to anesthetize a subject (locally or generally). The subject's physical characteristics may also be important in determining the appropriate dosage. Characteristics such as weight, age, and the like may be important factors. For example, the anesthetic may have increased potency with age, as has been demonstrated in the case of the volatile anesthetic isoflurane.

The temperature of the volatile anesthetic may also be considered as a factor in selecting an appropriate dose, as the solubility of many anesthetics may be affected by the temperature of the anesthetic and/or aqueous solution. For example, increases in temperature may increase the solubility, and thus potency, of the active agent; this property has been demonstrated with certain anesthetic agents. The particular dosage may also be dependent on the dosing regime chosen. For example, the active agent may be delivered continuously or periodically. Conversely, the active agent may be administered as a single administration as a one-time event.

Volatile anesthetics (e.g., halogenated anesthetic compounds) may be infused in amounts leading to spinal fluid levels in the range of about 250 to about 50,000 nanograms/ml, depending on the anesthetic selected and the desired effect. In certain embodiments, a halogenated anesthetic or volatile anesthetic may be administered to achieve cerebrospinal fluid (CSF) concentration of from about 5 to about 500,000 nanograms/ml. While the dose range will vary depending on the compound selected and patient variability, it is generally true that lower doses such as from about 0.01 to about 10,000 nanogram/ml are more suitable for treating minor to moderate pain, while higher doses such as from about 10000 nanogram/ml to about 500,000 nanogram/ml or more are suitable for treating severe pain and inducing anesthesia. Of course, the doses may be given once (for a minor single occurrence of pain), repeatedly (for moderate or chronic pain), or continuously (for severe pain or anesthesia purposes). Combinations of these dosing regimes may also be used. For example, a subject suffering from severe pain may require continuous dosing with periodic additional dosing needed for breakthrough pain.

In embodiments where an anesthetic (e.g., a volatile anesthetic, isoflurane, etc.) is admixed with a solution, such as saline or an artificial CSF solution, the concentration of the volatile anesthetic may vary. For example, a solution may contain an anesthetic in a v/v ratio of from about 1 to about 99%, from about 10 to about 75%, from about 10 to about 50%, from about 20 to about 50%, about 50%, about 45%, about 40%, about 35%, about 30%, about 25%, about 20%, about 15%, about 10%, about 5% or any range derivable therein. In these embodiments, the anesthetic may be a volatile anesthetic, such as isoflurane, and the solution may be an artificial cerebrospinal fluid (ACSF) solution.

In various embodiments and as shown in the below examples, a solution of about 10% volatile anesthetic, such as isoflurane, may be used; this solution may be administered as a bolus injection, continuously, and/or repeatedly to achieve analgesia and/or anesthesia. Thus, as demonstrated in the below examples, a 10% v/v solution of a volatile anesthetic may be used to induce analgesia. Higher concentrations of volatile anesthetic may be used, in various embodiments, to induce a regional anesthesia.

Method of Active Agent Delivery

Anesthetics of the present invention may be delivered regionally or locally. "Regional" or "local" anesthesia, as used herein, is distinct from general anesthesia and refers to anesthetic procedures which allow for the preferential delivery of an anesthetic to a specific region of the body, such as near a nerve or a nerve bundle. In contrast, general anesthesia allows for the systemic administration of an anesthetic, e.g., via intravenous administration. Regional or local anesthesia typically allows for a lower total body concentration (although elevated local concentrations) of an anesthetic to be administered to a subject for analgesia or diminished pain perception of at least a portion of the subject's body. For example, intrathecal anesthesia, epidural anesthesia, and nerve blocks are examples of regional or local anesthesia. Specific concentrations of anesthetics which may be used for regional or local anesthesia include from about 250 to about 50,000 nanogram/ml, from about 250 to about 25000 nanogram/ml, from about 250 to about 10000 nanogram/ml, from about 250 to about 5000 nanogram/ml, from about 250 to about 2500 nanogram/ml, or from about 250 to about 1000 nanogram/ml.

The present invention may be used with various nerve block procedures. Nerve block procedures according to the present invention may be performed with or without ultrasound visualization; for example, an ultrasound machine may be used to visualize the region of the body involved a the nerve block procedure, such as, e.g., various nerve bundles in the shoulder, neck, lower back, etc. The inventors envision that the present invention may be used in conjunction with a hip replacement, shoulder replacement, and/or birthing-related procedures.

In certain embodiments, compositions and methods of the present invention may be used for pain management. Pain management is distinct from general anesthesia in that a lower total body concentration of an anesthetic may be administered to a subject to in order to increase analgesia or decrease perception of pain, preferably without rendering the subject unconscious. Specific concentrations of anesthetics which may be used for pain management include from about 250 to about 50,000 nanogram/ml, from about 250 to about 25000 nanogram/ml, from about 250 to about 10000 nanogram/ml, from about 250 to about 5000 nanogram/ml, from about 250 to about 2500 nanogram/ml, or from about 250 to about 1000 nanogram/ml.

Epidural or intrathecal administration of an anesthetic may be accomplished via techniques known in the art, such as the use of an intrathecal or epidural catheter. The catheter should be placed closer to the nerves critical for the propagation of any pain sensory information which the practitioner desires to inhibit, without damaging the nerves.

Other routes of administration which are contemplated include: injection, infusion, continuous infusion, localized perfusion bathing target cells directly, via a catheter, via nanoparticle delivery, topical administration (e.g., in a carrier vehicle, a topical control release patch), intra-articular, intravenous and/or oral administration. An appropriate biological carrier or pharmaceutically acceptable excipient may be used. Compounds administered may, in various embodiments, be racemic, isomerically purified, or isomerically pure.

In certain embodiments, anesthetics of the present invention are not administered intravenously. Intravenous administration is often used for general anesthesia (Mathias et al. 2004) and typically results in the rapid distribution of the anesthetic agent throughout the body of a subject. Thus, in certain embodiments, intravenous administration is incompatible for use with regional or local anesthesia.

FIG. 1 provides a flowchart depiction of a general method for delivering a halogenated ether anesthetic. As shown in FIG. 1, method (100) begins with the selection of an halogenated ether compound (102). The halogenated ether anesthetic may be a standard volatile anesthetic gas, or an active agent that is capable or reducing pain and of becoming readily gaseous, as described above.

Solutions

After a halogenated ether anesthetic has been selected, it may be dissolved into a solution (104). The solution may be an aqueous solution, such as saline, artificial cerebrospinal fluid, the subject's own cerebrospinal fluid, or the like. In some variations, other solutions may be appropriate.

Various formulations of saline are known in the art and may be used with the present invention. For example, the saline may be lactated Ringer's solution, acetated Ringer's solution, phosphate buffered saline (PBS), Dulbecco's phosphate buffered saline (D-PBS), Tris-buffered saline (TBS), Hank's balanced salt solution (HBSS), or Standard saline citrate (SSC).

The saline solutions of the present invention are, in certain embodiments, "normal saline" (i.e., a solution of about 0.9% w/v of NaCl). Normal saline has a slightly higher degree of osmolality compared to blood; however, in various embodiments, the saline may be isotonic in the body of a subject such as a human patient. Normal saline (NS) is often used frequently in intravenous drips (IVs) for patients who cannot take fluids orally and have developed severe dehydration. In certain embodiments, "half-normal saline" (i.e., about 0.45% NaCl) or "quarter-normal saline" (i.e., about 0.22% NaCl) may be used with the present invention. Optionally, about 5% dextrose or about 4.5 g/dL of glucose may be included in the saline. In various embodiments, one or more salt, buffer, amino acid and/or antimicrobial agent may be included in the saline.

Various artificial cerebrospinal fluid (ACSF) solutions may be used with the present invention. In certain embodiments, the ACSF is a buffered salt solution (pH 7.4) with the following composition (in mM): NaCl, 120; KCl, 3; NaHCO$_3$, 25; CaCl$_2$, 2.5; MgCl$_2$, 0.5; glucose, 12. ACSF can also be obtained from various commercial sources, such as from Harvard Apparatus (Holliston, Mass.).

In various embodiments, a preservative or stabilizer may be included in the composition or solution. For example, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof. Agents which may be included suitable for injectable use include sterile aqueous solutions or dispersions and sterile powders for the extemporaneous preparation of sterile injectable solutions or dispersions (U.S. Pat. No. 5,466,468, specifically incorporated herein by reference in its entirety). In all cases the composition is preferably sterile and must be fluid to facilitate easy injectability. Solutions are preferably stable under the conditions of manufacture and storage and must be preserved against the contaminating action of microorganisms, such as bacteria and fungi. Examples of stabilizers which may be included include buffers, amino acids such as glycine and lysine, carbohydrates such as dextrose, mannose, galactose, fructose, lactose, sucrose, maltose, sorbitol, mannitol, etc. Appropriate stabilizers or preservatives may be selected according to the route of administration desired.

The weight ranges of compounds in the solution may vary. For example, in various embodiments, the composition may comprise about 1-5 wt % anesthetic agent, about 1-5 wt % preservative/stabilizer, about 1-5 wt % NaCl, and about 85%-97% water. The ratio of anesthetic to water may be varied as needed to achieve the desired effect (pain reduction or analgesia, regional anesthesia, etc.).

The solution and/or composition may also be sterilized prior to administration. Methods for sterilization are well known in the art and include heating, boiling, pressurizing, filtering, exposure to a sanitizing chemical (e.g., chlorination followed by dechlorination or removal of chlorine from solution), aeration, autoclaving, and the like.

The active agent gas may be dissolved into the solution in any number of ways. For example, it may be bubbled through the solution, e.g., using a vaporizer, or it may be solubilized by agitation. In certain embodiments, an anesthetic such as a halogenated ether or a volatile anesthetic may be measured in liquid form and directly admixed into a solution. Of course, other suitable methods of dissolving the anesthetic into solution may also be used. After the halogenated ether anesthetic has been solubilized, it may be administered to a subject in need of pain reduction (including pain reduction in the form of anesthesia) epidurally or intrathecally (FIG. 1, 106) using techniques well known in the art. In certain embodiments, a volatile anesthetic is admixed with a solution in a closed vacuum container, and the combined solutions are then mechanically agitated for 3-5 minutes and held in a thermo-neutral sonicator until use.

In preferred embodiments, solutions of the present invention are essentially free of oil-in-water emulsions such as soybean emulsion. Oil-in-water emulsions may alter the pharmacokinetics and/or distribution of an anesthetic, which may not be desirable in certain instances. Additionally, in various embodiments, oil-in-water emulsions are not desirable for intrathecal or epidural applications, as a practitioner may not wish to inject oil into the spinal canal. Saline, artificial CSF, or the patients own CSF may be used for intrathecal or epidural administration of an anesthetic according to the present invention. Lipid emulsions also have other drawbacks and risks. For example, depending on the route, lipid emulsions can cause pain and irritation upon injection. Lipid emulsions also pose a not insubstantial risk of infection, as has been observed in the past with bacterially contaminated propofol emulsions. The present invention addresses these limitations by providing solutions which can reduce pain perception upon injection and may have a reduced risk of contamination.

Pharmaceutical compositions of the present invention comprise an effective amount of one or more anesthetic or biologically active gas or additional agent dissolved or dispersed in a pharmaceutically acceptable carrier. The phrases "pharmaceutical or pharmacologically acceptable" refers to molecular entities and compositions that do not produce an adverse, allergic or other untoward reaction when administered to an animal, such as, for example, a human, as appropriate. The preparation of an pharmaceutical composition that contains at least one anesthetic or biologically active gas in solution or additional active ingredient will be known to those of skill in the art in light of the present disclosure, as exemplified by *Remington: The Science and Practice of Pharmacy,* 20th Edition (2000), which is incorporated herein by reference. Moreover, for animal (e.g., human) administration, it will be understood that preparations should meet sterility, pyrogenicity, general safety and purity standards as required by FDA Office of Biological Standards.

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example I

Intrathecal Administration of Isoflurane and Sevoflurane

This study was designed to evaluate efficacy of direct intrathecal injection of anesthetic agent gases in reducing pain and providing analgesia. The study was conducted over a one (1) month period using anesthetic gases isoflurane and sevoflurane injected directly intrathecally or dissolved in saline as shown in the studies below. The subject animal used was the rat, since the rat has a well-established model of pain/analgesia testing. In particular, Sprague-Dawley rats weighing over 350 gm were used. The rats were anesthetized with pentobarbital (50 mg/kg), and the anesthetic depth of the animals was determined by corneal reflex and paw withdrawal reflex to a noxious stimulus.

The neck of the rats were shaved and cleaned with disinfectant solutions in order to avoid bacterial contamination during surgery. A midline surgical dissection of the posterior neck muscles was performed to obtain access to the occipito-atlantoid membrane. This membrane was identified and then dissected. A sterile polyethylene catheter was introduced in the subarachnoid space until the lumbar enlargement of the spinal cord (approximately 7-8 cm measured in each animal). The surgical wound was closed, first suturing the neck muscles with 3-0 silk sutures and then closing the skin incision with staples.

After the surgery, the rats were moved to their cages and a radiant lamp was placed over the cages so that the rats would not undergo anesthetic-induced hypothermia. The rats were continuously monitored from the end of the surgery until they were fully awake. Rats showing any motor impairment after surgery were euthanized.

On the fifth day after surgery, those rats without wound infection or motor dysfunction were transported to the pain behavioral lab to enter the intrathecal study with volatile anesthetics. 12 rats were selected for the study. All these rats had intrathecal catheters. Isoflurane (1-chloro-2,2,2-trifluoroethyl difluoromethyl ether) and sevoflurane (fluoromethyl 2, 2, 2-trifluoro-1-(trifluoromethyl)ethyl ether) were used as the halogenated ether compounds. Both of these are halogenated volatile anesthetic agents, with isoflurane manufactured by Baxter and sevoflurane manufactured by Abbott Laboratories. The 12 rats were divided into 3 groups of four rats each for study A and B.

In the first group, 2 microliters of preservative-free normal saline was injected via the intrathecal catheter into each rat. This catheter was then flushed with preservative-free normal saline. Pain behavioral testing on this group was then performed.

In the second group, 2 microliters of isoflurane was injected via the intrathecal catheter into each rat. This catheter was also flushed with preservative-free normal saline. This group was then subjected to pain behavioral testing.

In the third group, 2 microliters of sevoflurane was injected via the intrathecal catheter into each rat. This catheter was also flushed with preservative-free normal saline. This group was then subjected to pain behavioral testing.

A "hotplate" behavioral test was used to evaluate pain perception and analgesia. The pain behavioral testing model used in these studies have been well established by Tony Yaksh. (See, e.g. Chaplan et al., 1994; Yaksh et al., 2001; Kim and Chung, 1992; Sorkin et al., 2001). This test involves determining how quickly a rat will withdraw its hind paw in response to a noxious stimulus such as a radiant heat source placed directly underneath its paw. This time for withdrawal is known as "thermal withdrawal latency".

Rats were transferred for testing onto a modified Hargreaves apparatus with a heated glass plate maintained at 25° C. (see Hargreaves et al., 1988). A focused projection bulb below the plate was aimed at the mid-plantar surface of the paw. A photodiode-activated timer measured the withdrawal latency, and a cutoff time of 25 seconds was used to prevent tissue damage. Thermal withdrawal latency to radiant heat was measured at 5 minutes and 30 minutes after each intrathecal injection. Each paw was tested three times, and the results were averaged. The below data was collected for both the right and left hind paws:

Group 1: Control Group (Normal Saline) Tested at 5 Minutes

|  | Test 1 | | Test 2 | | Test 3 | | |
| --- | --- | --- | --- | --- | --- | --- | --- |
|  | Right | Left | Right | Left | Right | Left | Average |
| Rat 1: | 9.00 | 9.26 | 10.45 | 6.74 | 8.42 | 9.95 | 8.97 |
| Rat 2: | 11.23 | 9.32 | 6.34 | 7.98 | 10.65 | 8.73 | 7.19 |
| Rat 3: | 7.83 | 8.21 | 9.67 | 11.90 | 8.55 | 6.38 | 8.76 |
| Rat 4: | 9.72 | 8.04 | 6.77 | 8.92 | 7.88 | 8.95 | 8.38 |
|  |  |  |  |  | Group 1 Average: | | 8.33 seconds |

Group 2 Study A: Isoflurane Group Tested at 5 Minutes

|  | Test 1 | | Test 2 | | Test 3 | | |
| --- | --- | --- | --- | --- | --- | --- | --- |
|  | Right | Left | Right | Left | Right | Left | Average |
| Rat 5: | 19.81 | 17.23 | 20.38 | 18.91 | 20.34 | 18.82 | 19.25 |
| Rat 6: | 17.19 | 19.24 | 15.88 | 17.65 | 18.59 | 20.72 | 18.21 |
| Rat 7: | 19.20 | 18.11 | 17.90 | 19.80 | 16.71 | 20.07 | 18.63 |
| Rat 8: | 20.31 | 19.71 | 18.34 | 17.18 | 16.75 | 16.38 | 17.95 |
|  |  |  |  |  | Group 2 Average: | | 18.51 seconds |

Group 3 Study B: Sevoflurane Group Tested at 5 Minutes

|  | Test 1 | | Test 2 | | Test 3 | | |
| --- | --- | --- | --- | --- | --- | --- | --- |
|  | Right | Left | Right | Left | Right | Left | Average |
| Rat 9: | 13.81 | 14.90 | 13.23 | 15.11 | 16.03 | 14.83 | 14.65 |
| Rat 10: | 17.19 | 13.38 | 14.29 | 12.31 | 13.75 | 12.01 | 13.82 |
| Rat 11: | 14.98 | 12.34 | 13.93 | 11.03 | 12.37 | 14.16 | 13.14 |
| Rat 12: | 10.31 | 11.83 | 13.20 | 12.66 | 17.59 | 12.31 | 12.98 |
|  |  |  |  |  | Group 3 Average: | | 13.65 seconds |

These rats were then allowed time to recover from their intrathecal injection. There were no apparent adverse effects such as respiratory depression, cardiac, or neurological compromise. At 30 minutes after the injection, the rats were tested again, according to grouping:

Group 1: Control Group (Normal Saline) Tested at 30 Minutes

|  | Test 1 | | Test 2 | | Test 3 | | |
| --- | --- | --- | --- | --- | --- | --- | --- |
|  | Right | Left | Right | Left | Right | Left | Average |
| Rat 1: | 7.32 | 8.02 | 9.17 | 8.64 | 5.89 | 7.71 | 7.79 |
| Rat 2: | 6.77 | 5.98 | 7.81 | 6.54 | 9.03 | 8.20 | 8.59 |
| Rat 3: | 7.08 | 8.39 | 7.26 | 8.49 | 9.23 | 9.84 | 8.38 |
| Rat 4: | 8.36 | 9.44 | 9.15 | 9.67 | 8.54 | 7.92 | 8.85 |
|  |  |  |  |  | Group 1 Average: | | 8.40 seconds |

Group 2, Study A: Isoflurane Group Tested at 30 Minutes

|  | Test 1 | | Test 2 | | Test 3 | | |
| --- | --- | --- | --- | --- | --- | --- | --- |
|  | Right | Left | Right | Left | Right | Left | Average |
| Rat 5: | 9.87 | 9.12 | 10.59 | 9.02 | 8.54 | 9.77 | 9.48 |
| Rat 6: | 9.08 | 6.35 | 7.81 | 8.22 | 10.49 | 11.62 | 8.93 |
| Rat 7: | 6.32 | 8.37 | 9.48 | 8.45 | 11.03 | 10.48 | 10.52 |
| Rat 8: | 9.41 | 10.27 | 6.76 | 7.04 | 7.88 | 10.32 | 9.21 |
|  |  |  |  |  | Group 2 Average: | | 9.53 seconds |

Group 3. Study B: Sevoflurane Grout Tested at 30 Minutes

|  | Test 1 | | Test 2 | | Test 3 | | |
| --- | --- | --- | --- | --- | --- | --- | --- |
|  | Right | Left | Right | Left | Right | Left | Average |
| Rat 9: | 9.23 | 8.54 | 7.30 | 8.29 | 9.43 | 8.87 | 8.61 |
| Rat 10: | 7.38 | 6.87 | 8.92 | 7.99 | 10.83 | 8.10 | 8.35 |
| Rat 11: | 10.05 | 8.44 | 9.32 | 11.74 | 7.66 | 6.13 | 8.89 |
| Rat 12: | 9.55 | 10.93 | 8.67 | 6.68 | 9.27 | 12.11 | 9.54 |
|  |  |  |  |  | Group 3 Average: | | 8.84 seconds |

The results of this study demonstrated the efficacy of intrathecal administration of volatile anesthetic agents in reducing pain. At the smallest intrathecally delivered dose of 2 microliters, an analgesic effect of isoflurane and sevoflurane was shown. The thermal latency time was significantly increased, thus showing that the thermal C-fiber pain pathway was effectively dampened. This study also shed some light into the safety of intrathecally delivering active agent gases. None of the rats in the study experienced adverse effects, and all of them fully recovered from the intrathecal injection after 30 minutes, as indicated by the return to thermal latency baseline for all groups.

Example II

Preparation of a 5 µL Sample of Isoflurane Dissolved in Saline

Isoflurane was dissolved into saline using the following method (also referred to as the "bubbling" method). Study C: A mock vaporizing device was created using a 500 ml modified Erlenmeyer flask (2 inlets and 1 catheter into the liquid phase). The flask was partially filled with 0.9% normal saline and a stoppered glass pipette was inserted into the bottom of the liquid phase for injection of isoflurane. A second egress pipette allowed egress of gas from the closed container. 2% isoflurane solution in oxygen at 2 L/min was injected through the pipette, saturating the 0.9% saline solution after approximately 10 minutes of injection. 5 mL was drawn from the saturated saline solution and administered to 10 animals using the procedures outlined in Example I above.

For study C, all animals were prepared as for experiments A and B. The inventors injected 4 animals with 5 microliter of dissolved isoflurane solution (as prepared in 0030) via intrathecal catheter. Note, control (baseline) latency to paw withdrawal is different in Study C due to a different intensity of heat lamp used. Each animal serves as its own control in study C.

Figure 2:
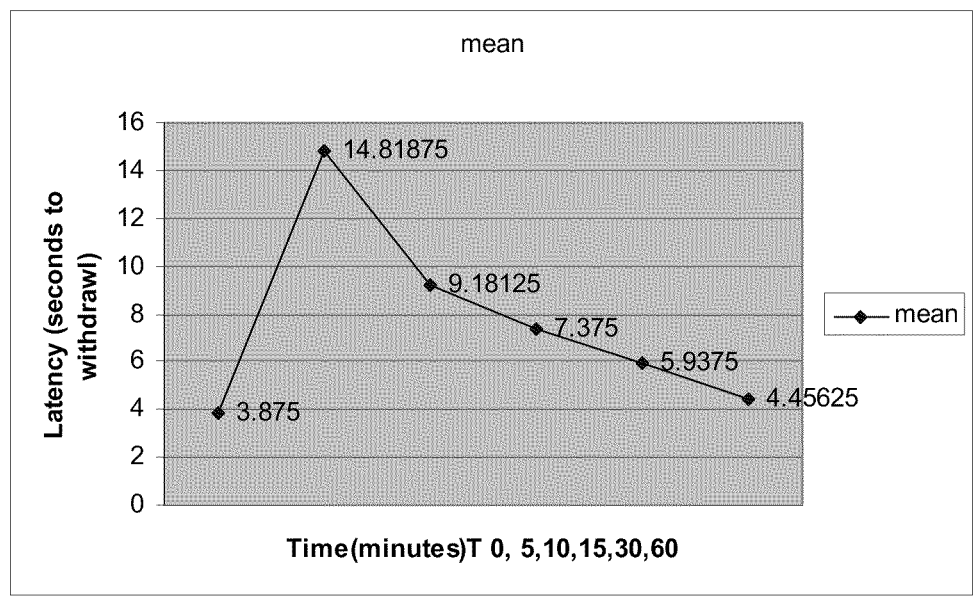
FIG. 2: Inhibition of pain via intrathecal administration of isoflurane solution as measured using the hotplate test.

Study C Data is presented here: in seconds to paw withdrawal to heat source. Table and graphic format. Results are shown in FIG. 2.

|        | CONTROL  | 5 MIN    | 10 MIN   | 15 MIN   | 30 MIN   | 60 MIN   |
|--------|----------|----------|----------|----------|----------|----------|
| RAT 1  | 4.8      | 11       | 5.4      | 7.6      | 6.8      | 6.1      |
|        | 4.4      | 15       | 9        | 7.3      | 7.2      | 5.8      |
|        | 4.8      | 19.5     | 9        | 8.8      | 4.9      | 5.1      |
|        |          | 20       | 6.8      | 7        | 5.2      | 4.9      |
| RAT 2  | 3.4      | 10.9     | 9.9      | 10.4     | 8.2      | 3.8      |
|        | 4.3      | 12.6     | 8.7      | 9.4      | 6.9      | 4.7      |
|        | 3.6      | 18.1     | 12       | 5.4      | 8.1      | 7        |
|        |          | 17.3     | 9        | 13.4     | 6.4      | 4.1      |
| RAT 3  | 3.6      | 14.2     | 12.2     | 6.1      | 5.2      | 4.2      |
|        | 3.8      | 20       | 12       | 7.1      | 6.1      | 3.5      |
|        | 4.7      | 20       | 9.1      | 4.8      | 5.8      | 3.3      |
|        |          | 16       | 8.9      | 5.2      | 6.5      | 3.8      |
| RAT 5  | 3.9      | 9.8      | 8.8      | 7.9      | 4.9      | 4.2      |
|        | 2.6      | 11.8     | 7.8      | 6.4      | 4.3      | 3.5      |
|        | 2.6      | 9.1      | 10.2     | 6.9      | 4.7      | 3.8      |
|        |          | 11.8     | 8.1      | 4.3      | 3.8      | 3.5      |
| mean   | 3.875    | 14.81875 | 9.18125  | 7.375    | 5.9375   | 4.45625  |
| SD     | 0.767671 | 3.809235 | 1.77067  | 2.231171 | 1.266331 | 1.073293 |

Example III

Intrathecal Inhibition of Pain Using Isoflurane Dissolved in Artificial Cerebrospinal Fluid Pain sensitivity was measured after intrathecal administration of isoflurane in artificial cerebrospinal fluid (ACSF). Further, as detailed below, the isoflurane was first dissolved in ACSF and then sonicated before administration. The dose response relationship was then evaluated by generating a stimulus-response (SR) graph in order to determine relevant concentrations of isoflurane that may be administered intrathecally to achieve analgesia or anesthesia. The characterization of the pharmacological profile of intrathecal administration of isoflurane in ACSF was performed in this example using rats; further, as would be appreciated by one of skill in the art, analogous approaches may be used to determine the precise pharmacological profile in humans.

Isoflurane dissolved in ACSF was prepared by the following method. Isoflurane was admixed in a closed vacuum container in a v/v ratio of 10-50% with buffered salt solution that approximates cerebrospinal fluid (pH 7.4) with the following composition (in mM): NaCl, 120; KCl, 3; NaHCO$_3$, 25; CaCl$_2$, 2.5; MgCl$_2$, 0.5; glucose, 12. The combined solutions were mechanically agitated for 3-5 min and then held in a thermo-neutral sonicator until use.

The solutions of isoflurane in ACSF were then administered to rats intrathecally via the following method. Treatment solution is delivered via intrathecal catheter that overlies lumbar segment L1-2 in a volume of 10 µl followed by a 10 µl flush of ACSF.

Pain perception was tested after intrathecal administration of isoflurane dissolved in artificial CSF using the "hotplate" behavioral test, as described above, with the modification that a cutoff time of 20 seconds was used. As stated above the "hotplate" behavioral test involves testing the hind paw withdrawal threshold to radiant heat (i.e., duration of time between before a rat to lifts a paw away from a heat source).

Figure 3:
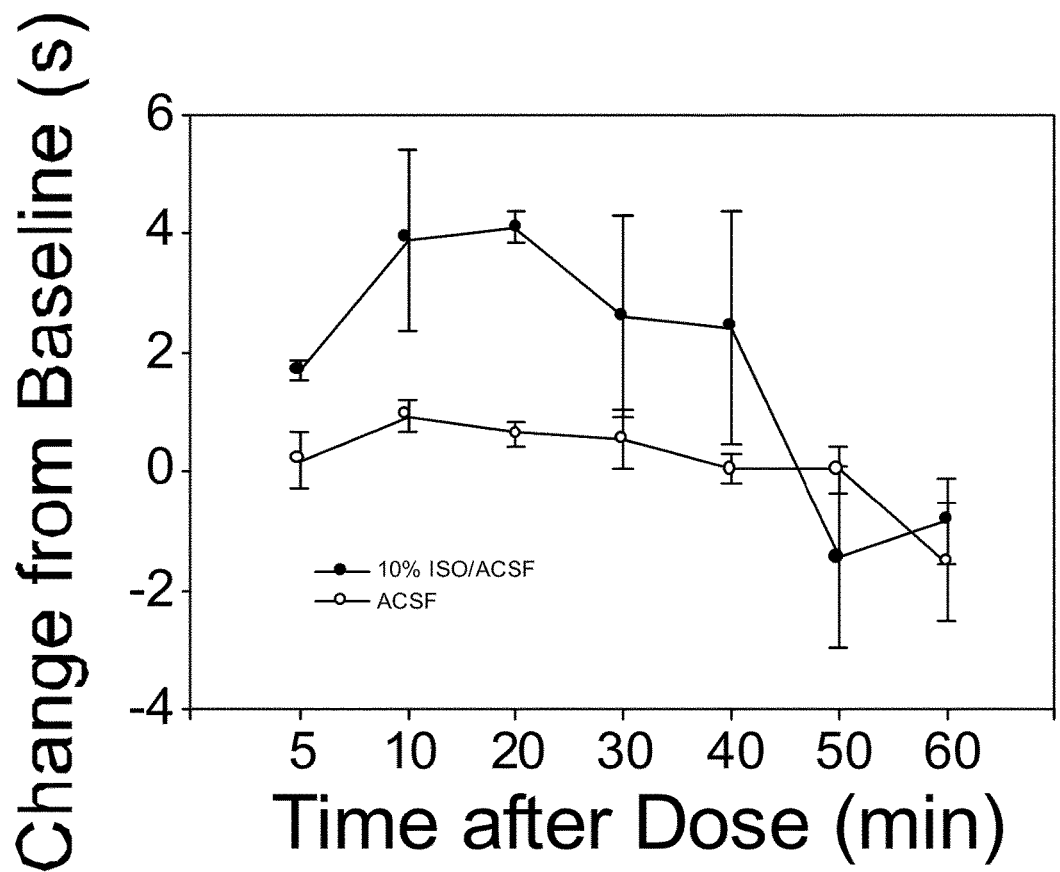
FIG. 3: Inhibition of pain using intrathecal isoflurane in artificial cerebrospinal fluic (ACSF). The time course for paw withdrawal from a hotplate after administration of isoflurane-ACSF, at a dose of 1.46 mg isoflurane, is shown.

Intrathecal administration of isoflurane in ACSF resulted in analgesia. As shown in FIG. 3, intrathecal administration of isoflurane in ACSF (i.e., at a 1.46 mg dose of isoflurane) resulted in analgesia as measured by testing the hind paw withdrawal threshold to radiant heat. A 10 µL solution of isoflurane in ACSF (10% v/v) was used. As described below, this dose of isoflurane represents a moderate dose of intrathecal isoflurane.

Figure 4:
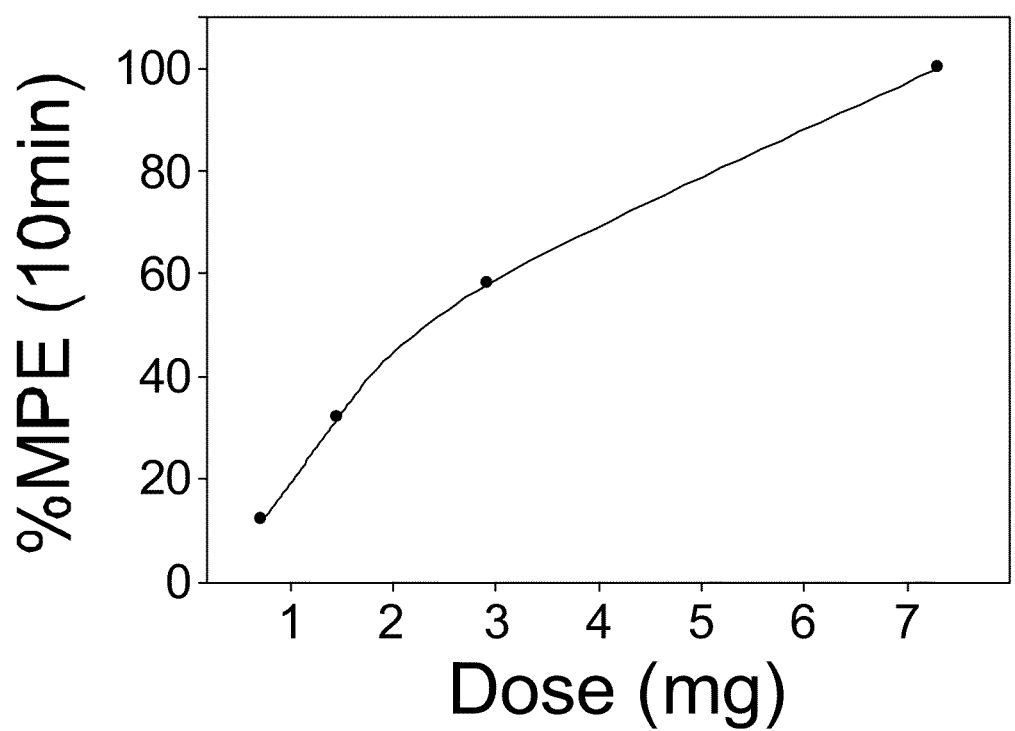
FIG. 4: A stimulus response (SR) graph is shown of the maximal possible effect (MPE) by dose for the time point of 10 minutes after intrathecal injection of isoflurane-ACSF.

The dose response relationship was then evaluated by generating a stimulus-response (SR) graph in order to standardize responses across animals and determine relevant concentrations of isoflurane that may be administered intrathecally to achieve analgesia or anesthesia. FIG. 4 shows an stimulus-response (SR) graph of the maximal possible effect (MPE) by dose for the time point of 10 minutes after the injection of isoflurane in ACSF. Various doses of isoflurane are shown on the x-axis; for example, the 10% v/v solution of isoflurane used above, as shown in FIG. 3, corresponds to approximately a 34% MPE as shown in FIG. 4. MPE is used here to standardize responses across animals. MPE is calculated as ((drug response time—baseline response time)/(cutoff time−baseline response time))*100. The cutoff time used here was 20 seconds. As shown in FIG. 4, a substantial analgesic effect was observed.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Chaplan et al., *J. Neurosci. Methods,* 53:55-63, 1994.
Hargreaves et al., *Pain,* 32:77-88, 1988.
Kim and Chung, *Pain,* 50:355-363, 1992.
Mathias et al., *Revista Brasileira de Anestesiologia,* ISSN 0034-7094, 2004.
Moller et al., *Lancet.,* 351:857-861, 1998.
Rasmussen et al., *Acta Anaesthesiologica Scandinavica,* 47(3):260-266, 2003.

Remington: The Science and Practice of Pharmacy, 20th Ed., Baltimore, Md.: Lippincott Williams & Wilkins, 2000
Rogers et al., *BMJ,* 321:1-12, 2000.
Sorkin et al., *Anesthesiology,* 95:965-973, 2001.
Yaksh et al., *J. Appl. Physiol.,* 90:2386-2402, 2001.

What is claimed is:

1. A method for reducing pain perception in a mammalian subject in need of such pain reduction, the method consisting of topically administering to the skin of said subject a topical patch consisting of sevoflurane and one or more pharmaceutically acceptable carriers in an amount effective to reduce pain perception in the subject,
   wherein the administering does not result in general anesthesia in the subject, and wherein the subject is not under general anesthesia;
   wherein the topical administration results in analgesia;
   wherein the volatile anesthetic is the only analgesic agent present in the pharmaceutical preparation in an amount sufficient to reduce pain in said subject; wherein the topical administration is not by inhalation;
   and wherein said topical administration reduces pain perception in the subject.

2. The method of claim 1, wherein the method comprises treating chronic pain in the subject.

3. The method of claim 1, wherein the method comprises treating acute pain in the subject.

4. The method of claim 1, wherein the pharmaceutical preparation is delivered to anesthetize a portion of said subject prior to a surgery.

5. The method of claim 1, wherein the administration is periodic.

6. The method of claim 1, wherein the administration is a one-time event.

7. The method of claim 1, wherein the volatile anesthetic is periodically administered to the subject on separate occasions.

8. The method of claim 1, wherein the method results in elimination of pain perception of a portion of the body of the subject.

9. The method of claim 1, wherein the subject is a human.

10. The method of claim 1, wherein the subject is a mouse or a rat.

* * * * *